United States Patent
Ertl et al.

(10) Patent No.: US 11,254,959 B2
(45) Date of Patent: Feb. 22, 2022

(54) PROCESS FOR THE CONVERSION OF SUGARS

(71) Applicant: ANNIKKI GMBH, Raaba-Grambach (AT)

(72) Inventors: Ortwin Ertl, Vasoldsberg (AT); Bernd Mayer, Graz (AT); Nicole Staunig, Vasoldsberg (AT)

(73) Assignee: ANNIKKI GMBH, Raaba-Grambach (AT)

( * ) Notice: Subject to any disclaimer, the term of this patent is extended or adjusted under 35 U.S.C. 154(b) by 230 days.

(21) Appl. No.: 16/304,089

(22) PCT Filed: May 18, 2017

(86) PCT No.: PCT/EP2017/061978
§ 371 (c)(1),
(2) Date: Nov. 21, 2018

(87) PCT Pub. No.: WO2017/202686
PCT Pub. Date: Nov. 30, 2017

(65) Prior Publication Data
US 2020/0325511 A1    Oct. 15, 2020

(30) Foreign Application Priority Data
May 23, 2016  (EP) .................................. 16170892

(51) Int. Cl.
*C12P 19/02* (2006.01)
*C12P 7/18* (2006.01)
*C12P 7/58* (2006.01)

(52) U.S. Cl.
CPC ............... *C12P 19/02* (2013.01); *C12P 7/18* (2013.01); *C12P 7/58* (2013.01)

(58) Field of Classification Search
None
See application file for complete search history.

(56) References Cited

U.S. PATENT DOCUMENTS

2018/0216142 A1 *  8/2018  Ertl .......................... C12P 7/18

FOREIGN PATENT DOCUMENTS

EP          0132557 A2 *  2/1985
WO    WO2013117585           8/2013

OTHER PUBLICATIONS

Lindstad et al., "Effect of pH on sheep liver sorbitol dehydrogenase steady-state kinetics", Eur. J. Biochem., 1995, vol. 233, pp. 891-898.*
Ikemi, M. et al.: "Sorbitol Production in Charged Membrane Bioreactor with Coenzyme Regeneration System: I . Selective Retainment of NADP(H) in a Continuous Re action" Biotechnology and Bioengineering, vol. 36, No. 2, Jun. 20, 1990 (Jun. 20, 1990).
Nidetzky, B. et al.: "Continuous Enzymatic Production of Xylitol with Simultaneous Coenzyme Regeneration in a Charged Membrane Reactor", A 1-14 Biotechnology and Bioengineering, vol. 52, No. 3, 1996, pp. 387-396.
International Search Report issued in PCT/EP2017/061978 dated Aug. 1, 2017.

* cited by examiner

*Primary Examiner* — Suzanne M Noakes
(74) *Attorney, Agent, or Firm* — Workman Nydegger

(57) ABSTRACT

The present invention relates to a process for the conversion of D-glucose. The process according to the invention comprises a step a) in which part of the D-glucose is enzymatically oxidized to D-gluconic acid (lactone) and a portion of the D-glucose which is essentially equimolar thereto is reduced to D-sorbitol. In addition to D-glucose, D-fructose is also present in the reaction mixture of step a). The process comprises a further step b) in which D-sorbitol formed from the D-glucose in step a) is enzymatically oxidized to D-fructose.

20 Claims, 2 Drawing Sheets

D-glucose          D-sorbitol    D-gluconic acid

D-glucose          D-sorbitol   D-gluconic acid     D-fructose   D-gluconic acid D-fructose   D-glucose                    D-fructose   D-sorbitol   D-gluconic acid D-fructose   D-glucose          D-fructose   D-sorbitol   D-gluconic acid D-fructose   D-gluconic acid

PROCESS FOR THE CONVERSION OF SUGARS

The present invention relates to a process for the conversion of D-glucose.

INTRODUCTION

Because of the costs of fossil raw materials which are rising in the long run and a decline in the supply of such raw materials which is to be expected, there is a lot of interest in the utilization of renewable raw materials. In this connection, a distinction must be made between the field of energy production and that of the production of foodstuff and basic chemicals. The present invention relates to the latter two fields and concerns a process for the conversion of D-glucose.

In nature, D-glucose can occur as a monomeric sugar or as part of disaccharides such as, e.g., sucrose, maltose or lactose. Besides, D-glucose is abundant in various biopolymers, which are components of renewable raw materials. Suitable sources of D-glucose in a process according to the present invention include, for example, enzymatic or non-enzymatic hydrolysates of starch, especially corn starch, enzymatic or non-enzymatic hydrolysates of sucrose or enzymatic or non-enzymatic hydrolysates of cellulose. Cellulose used in a process according to the present invention can be obtained, for example, from biomass, preferably from lignocellulosic biomass such as, e.g., wood, straw, such as wheat straw, corn straw, bagasse, sisal, energy grasses. For the enzymatic hydrolysis of corn starch, amylases can be used, for example. For the enzymatic cleavage of sucrose, invertases are suitable, for example. For the enzymatic cleavage of cellulose, cellulases can be used, for example. Acid-catalyzed cleavage is suitable, for example, for the non-enzymatic cleavage of said multiple sugars.

PRIOR ART

A common way of converting D-glucose to D-fructose is by using an appropriate D-glucose isomerase, for example, D-xylose isomerase, which accepts D-glucose as a substrate. Such methods have long been known, for example, from U.S. Pat. No. 2,950,228, and are suitable also for industrial use, as described, for example, in U.S. Pat. No. 3,616,221 or 3,868,304.

A problem associated therewith is that, usually, a maximum amount of about 42% of the D-glucose can be converted to D-fructose (glucose-fructose syrup). A further accumulation of D-fructose relative to D-glucose can be achieved by separation methods. One possibility for this is the use of chromatographic methods, as described, for example, in U.S. Pat. No. 5,221,478. For the food sector, frequently, only a partial accumulation of D-fructose is aimed for. However, especially for the production of a relatively pure to highly pure D-fructose, chromatographic methods are very costly.

Another compound containing D-glucose is sucrose. It can be cleaved into the components D-glucose and D-fructose, e.g., by acid hydrolysis or enzymatically (invertase). A mixture of equal parts of glucose and fructose is thereby obtained. If one of the sugars is needed in pure form, further steps must be taken therein. In this connection, a similar (complex) approach as for glucose-fructose syrup is, for example, conceivable.

In addition to the use of isomerases, enzymatic redox reactions on carbohydrates have also been described in the literature.

For example, in DE 698 39 381, a sorbitol dehydrogenase is described which can be used for the conversion of D-sorbitol to L-sorbose and may be employed in the preparation of L-ascorbic acid.

In DE 10 247 147, a process is described in which D-fructose is reduced to D-mannitol using D-mannitol-2-dehydrogenase.

In U.S. Pat. No. 4,467,033, the enzymatic oxidation of L-sorbitol to L-fructose is described.

Examples of the reduction of D-xylose to xylitol are disclosed, for example, in US 2006/0035353 or in Woodyer R. et al., FEBS J., 2005, Volume 272, p 3816-3827.

Those processes are individual redox reactions which must be coupled with an additional reaction for the regeneration of redox cofactors with the addition of a further substrate.

In WO 2013/117584, a process is described by means of which glucose can be converted to fructose by way of enzymatic reduction and oxidation reactions. Fructose of very high purity can thereby be produced. However, a drawback associated therewith is that, for the reduction of glucose, a chemical, such as, e.g., an alcohol, must be added stoichiometrically or, respectively, to excess. This chemical is consumed during the reaction.

WO 2013/117585 describes a process in which glucose is enzymatically converted to fructose and the obtained fructose is converted to furan derivatives.

WO 2014/154676 describes a process in which glucose is enzymatically reduced to sorbitol and, subsequently, the obtained sorbitol is enzymatically oxidized to fructose.

According to WO 2014/122617, for the production of D-fructose from D-glucose, at first D-glucose is enzymatically oxidized to D-glucosone and then D-glucosone is enzymatically reduced to fructose.

From WO 2014/076012, an enzymatic process is known in which oxidation and reduction proceed simultaneously on sugars. However, in doing so, the equivalents for the oxidation of one sugar (arabinose) are obtained from the reduction of another sugar (xylose).

From the literature, a method is known in which xylose is reduced to xylitol, while glucose is simultaneously oxidized to gluconic acid (Nidetzky, B., Neuhauser, W., Haltrich, D., and Kulbe, K. (1996). Continuous enzymatic production of xylitol with simultaneous coenzyme regeneration in a charged membrane reactor. Biotechnology and Bioengineering 52, 387-396.). However, in doing so, the equivalents for the oxidation of one sugar (glucose) are obtained from the reduction of another sugar (xylose). In addition, xylose of the reaction mixture is mixed with glucose from an external source. So this is not about utilizing an existing mix. Furthermore, one has to rely on the fact that glucose and xylose are present stoichiometrically to each other in order to achieve a conversion as complete as possible.

Ikemi et al., *Biotechnology and Bioengineering*, 36 (1990), 149-154, describe the enzymatic production of sorbitol from glucose, whereby gluconic acid is simultaneously recovered in a bioreactor with a charged membrane.

An industrial process exists for the catalytic hydrogenation of glucose to sorbitol using hydrogen. However, in U.S. Pat. No. 3,329,729 A, a major drawback of this unselective process becomes apparent: other sugars (such as, e.g., fructose) in the mixture are also reduced to the respective sugar alcohol. Furthermore, only one product (sorbitol) can be produced from glucose.

For the production of gluconic acid from glucose, fermentative methods have, for example, been described (Example: Znad H., Markos J., and Báles V. (2004) Production of gluconic acid from glucose by *Aspergillus niger*. Process Biochemistry 39(11), 1341-1345.). Thereby, however, only one product (gluconic acid) can be produced from glucose.

Also for the production of uniform products from a mixture containing D-glucose and D-fructose using redox enzymes, there are already examples in the prior art. One possibility is the complete conversion of the glucose contained in the mixture with fructose to form gluconic acid. Said acid can subsequently be separated (e.g., by ion exchange chromatography). In addition to fermentative methods for producing D-gluconic acid (in a mixture of D-glucose and D-fructose), methods are also known in which the operation is done with isolated enzymes (e.g., U.S. Pat. No. 3,935,071A, GB 916 949A) or in which microorganisms are used which secrete suitable enzymes (e.g., FR 2 588 568 A1). In all methods of this kind, the glucose serves merely for the production of gluconic acid. No other product such as, e.g., sorbitol and hence no additional fructose can be generated from glucose. Thus, the glucose cannot be used for increasing the fructose yield in those methods.

Another possibility of producing a uniform product from glucose-fructose mixtures is the use of the enzyme glucose-fructose oxidoreductase. Said enzyme can be used either in its starting organism (often *Zymomonas mobilis*) or as an isolated or, respectively, recombinant enzyme (e.g., JPH01107145A; Zachariou M., and Scopes R. K. (1986) Glucose-fructose oxidoreductase, a new enzyme isolated from *Zymomonas mobilis* that is responsible for sorbitol production. J. Bacteriol 167(3), 863-869.). This entails the disadvantage that fructose is consumed in the process. The method is therefore not suitable for the production of fructose. Moreover, the glucose can be transformed completely into a product only in a stoichiometric mixture of glucose and fructose.

Another method of accumulating sugars has been described in U.S. Pat. No. 5,464,514. Therein, sugars are separated by way of their varying tendency to bind to a weak acid. The separation is then effected by electrodialysis. As the weak acid, boric acid is chosen, for example. Different sugars have different tendencies to bind to boric acid. The combination of sugar and boric acid is negatively charged and migrates in the electric field, while the sugars which do not bind to the boric acid remain uncharged. The electrodialysis cell is composed of a cathode and an anode between which two cation-exchange membranes have been attached. Between the two cation-exchange membranes, an anion-exchange membrane is located which divides the interspace into 2 compartments. Compartment I is located on the cathode side, and compartment II is located on the anode side. If a solution of the sugars to be separated is now introduced into compartment I and a voltage is applied, the negatively charged ions, i.e., the sugars which have bound to the boric acid, migrate through the anion-exchange membrane into compartment II. The uncharged sugars remain in compartment I. The method has been tested for the separation of lactose and lactulose as well as for the separation of glucose and fructose. However, this method is based on the fact that the affinity of the binding to boric acid differs between the sugars. However, part of the sugars with less affinity for boric acid will also bind the acid and thus move into compartment II. A separation of the sugars is thus not possible, only the ratio between the sugars will change. In the case of fructose and glucose, the ratio of the transfer rates is indicated as 1.4 to 1. The separation can be increased by several electrodialysis steps. Boric acid and sugar can subsequently be separated from each other in a further electrodialysis step. The disadvantage of the method is that proper separation can only be generated by many electrodialysis steps. In addition, this method does not distinguish between monomeric and dimeric or, respectively, oligomeric sugars. Proper separation can only be produced if the substances to be separated differ greatly in their affinity of binding to boric acid. Another disadvantage is that, with boric acid, an additional (toxic) component must be used.

The object of the present invention over the previously described prior art is to provide an improved process for the conversion of glucose and the recovery of valuable substances from glucose.

In one aspect, the present invention provides a process for the conversion of D-glucose which comprises a step a) in which a part of the D-glucose is enzymatically oxidized to D-gluconic acid (lactone) and a part of the D-glucose which is essentially equimolar thereto is enzymatically reduced to D-sorbitol, wherein, in addition to D-glucose, D-fructose is also present in the reaction mixture of step a) and wherein the process comprises a further step b) in which D-sorbitol formed from the D-glucose in step a) is enzymatically oxidized to D-fructose.

"Essentially equimolar" is understood to mean that the ratio of gluconic acid to sorbitol is between 0.9 and 1.1, preferably between 0.99 and 1.01, particularly preferably between 0.999 and 1.001. Those ratios relate exclusively to the products obtained by the reactions of step a). Other concentration ratios may occur in the solution if other reactions proceed concurrently (especially simultaneously), as will be shown hereinbelow.

Preferred embodiments of the process according to the invention are specified in the dependent claims.

Figure 1:
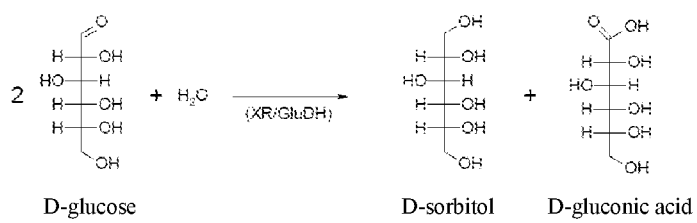
FIG. 1

Schematic illustration of the reactions of D-glucose to form D-gluconic acid (lactone) and D-sorbitol. For example, a xylose reductase having glucose reductase activity ("XR") and a glucose dehydrogenase ("GluDH") can be used as the enzymes.

FIG. 2

Schematic illustration of the reactions of D-glucose to form D-gluconic acid (lactone) and D-sorbitol and the further oxidation of D-sorbitol to D-fructose. For example, a xylose reductase having glucose reductase activity ("XR") and a glucose dehydrogenase ("GluDH") as well as a sorbitol dehydrogenase ("SDH") can be used as the enzymes.

FIG. 3

Schematic illustration of the reactions of D-glucose to form D-gluconic acid (lactone) and D-sorbitol in the presence of D-fructose. Example of a mixture of equal parts of D-glucose and D-fructose. Both with a lower and with a higher proportion of fructose, the reaction can be carried out analogously. For example, a xylose reductase having glucose reductase activity ("XR") and a glucose dehydrogenase ("GluDH") can be used as the enzymes.

FIG. 4

Schematic illustration of the reactions of D-glucose to form D-gluconic acid (lactone) and D-sorbitol in the presence of D-fructose and the further oxidation of D-sorbitol to D-fructose. Example of a mixture of equal parts of D-glucose and D-fructose. Both with a lower and with a higher proportion of fructose, the reaction can be carried out analogously. For example, a xylose reductase having glucose reductase activity ("XR") and a glucose dehydrogenase ("GluDH") as well as a sorbitol dehydrogenase ("SDH") can be used as the enzymes.

FIG. 5

Reaction scheme of the redox reactions of D-glucose to form D-gluconic acid (lactone) and D-sorbitol. The enzymatic reactions using redox cofactors are shown, as well as the mutual regeneration of the redox cofactors. Further conversion of the resulting sorbitol to fructose is possible.

DETAILED DESCRIPTION OF THE INVENTION

According to the present invention, a part of the D-glucose is enzymatically oxidized to D-gluconic acid (lactone) and a part of the D-glucose which is essentially equimolar thereto is enzymatically reduced to D-sorbitol. An important advantage associated therewith is that redox equivalents to the oxidation of glucose can be provided completely by the likewise occurring reduction of glucose and do not have to be supplied by additional measures such as, for example, the addition of additional substrates.

According to the invention, in addition to D-glucose, D-fructose is also present in the reaction mixture of step a). Furthermore, the process according to the invention comprises a further step b) in which D-sorbitol formed from the D-glucose in step a) is enzymatically oxidized to D-fructose.

Thus, the process according to the invention provides an elegant way of further accumulating fructose in mixtures of glucose and fructose and, on the other hand, of obtaining another value product (gluconic acid), which, moreover, can also be separated easily from the mixture.

In the process according to the invention, the D-fructose preferably remains essentially unchanged in step a) during the conversion of D-glucose to gluconic acid (lactone) or, respectively, sorbitol, i.e., it does not participate in the reaction.

In a particular aspect, a process according to the present invention is characterized in that the reaction mixture is contacted in step a) with a glucose dehydrogenase and a xylose reductase having glucose reductase activity or with another glucose reductase.

The amount of D-fructose in the mixture containing D-glucose and D-fructose can preferably be between 10% (w/w) and 95% (w/w), more preferably between 35% (w/w) and 90% (w/w), particularly preferably between 40% (w/w) and 60% (w/w), such as 42% (w/w), 50% (w/w) or 55% (w/w), based on the total amount of glucose and fructose. Such mixtures are obtainable, for example, as a glucose-fructose syrup prepared from corn starch or as an inverted sugar syrup by treatment of sucrose with invertase or a chemical hydrolysis such as, e.g., acid hydrolysis. Due to their natural origin, such solutions may also contain other substances such as, for example, other sugars.

A further particular embodiment of the process according to the present invention is characterized in that, in step b), the D-sorbitol is contacted with a sorbitol dehydrogenase for the enzymatic oxidation, whereby D-sorbitol is oxidized to D-fructose.

Enzymes and redox enzymes in a process according to the present invention include oxidoreductases. Oxidoreductases are enzymes that catalyze redox reactions. Oxidoreductases include, for example, dehydrogenases, reductases, oxidases, as well as catalases.

A particular embodiment of the process according to the present invention is characterized in that the redox cofactor(s) NAD(P)$^+$ and/or NAD(P)H is/are present in the reaction mixture of step a) and/or in the reaction mixture of step b). The redox cofactors can thus be present in only one of the two steps or also in both steps.

In this connection, NAD$^+$ denotes the oxidized form and NADH denotes the reduced form of nicotinamide adenine dinucleotide, whereas NADP$^+$ denotes the oxidized form and NADPH denotes the reduced form of nicotinamide adenine dinucleotide phosphate. If the enzyme preparations (e.g., lysates, solutions, lyophilisates, cell suspensions, whole-cell biocatalysts) already contain redox cofactors at sufficient concentrations addition of them is possibly not necessary. If the redox cofactors NAD(P)$^+$ and/or NAD(P)H is/are added during the conversion of D-glucose according to the present invention, the added concentration in a process according to the present invention usually ranges from 0.001 mM to 10 mM, preferably from 0.05 mM to 0.5 mM. In this case, the ratio of the molar concentration of the cofactor to the molar concentration of the sugars is at most 0.1, preferably at most 0.01, particularly preferably at most 0.001. For example, in a sugar solution of 50 mM, the cofactor concentration is usually limited to 5 mM or less.

During the conversion of D-glucose to D-gluconic acid (lactone) and D-sorbitol, no additional redox cofactor recycling is required, since the two reactions regenerate the redox cofactor mutually.

A further particular embodiment of the process according to the present invention is characterized in that, during the conversion of D-sorbitol to D-fructose, a reduced redox cofactor NADH/NADPH, which has been formed in step b), is enzymatically recycled back to its oxidized starting form continuously and in parallel.

In a particular aspect, a process according to the present invention is characterized in that, during the conversion of D-sorbitol to D-fructose, at least one redox cofactor is regenerated in step b) in the same reaction batch by at least one further redox enzyme, in particular selected from the group consisting of alcohol dehydrogenases, sugar dehydrogenases, NAD(P)H oxidases, hydrogenases or lactate dehydrogenases, whereby co-substrates, in particular ketones, aldehydes, sugars, pyruvic acid and its salts and/or oxygen, are consumed or, respectively, hydrogen is produced.

Furthermore, electrochemical processes for the regeneration of redox cofactors are described in the prior art (e.g., in Miyawaki O., and Yano T. (1997) Electrochemical bioreactor with regeneration of NAD$^+$ by rotating graphite disk electrode with PMS adsorbed. Enzyme Microb. Technol. 14, 474-478 or Maeda H., and Kajiwara S. (1985) Malic acid production by an electrochemical reduction system combined with the use of diaphorase and methylviologen. Biotechnol. Bioeng. 27(5), 596-602.). In principle, such processes are suitable for regenerating the cofactor reduced during the oxidation of sorbitol to fructose.

In a particular aspect, a process according to the present invention is further characterized in that D-sorbitol is converted to D-fructose in step b) in an enzymatic process, using and regenerating the redox cofactors NAD$^+$/NADH or NADP$^+$/NADPH, wherein, in the regeneration reaction, which converts the reduced redox cofactor back to its original oxidized form, oxygen, an aldehyde, a ketone, a sugar or a compound of the general formula

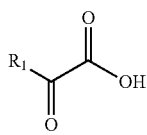

is reduced, wherein $R_1$ represents a straight-chain or branched-chain $(C_1\text{-}C_4)$-alkyl group or a $(C_1\text{-}C_4)$-carboxyalkyl group.

Moreover, a particular embodiment of the process according to the present invention is characterized in that steps a) and b) occur in the same reaction batch without the intermediate D-sorbitol being isolated.

The term "in the same reaction batch" is understood to refer to reactions which proceed in a reaction mixture without the need to isolate intermediates. In doing so, the reactions can proceed simultaneously or consecutively. The formulation involves that further components are added or removed during the reaction, but with educt, intermediate(s) and product of the reaction path D-glucose>D-sorbitol>D-fructose remaining in the solution until the reaction(s) is/are completed.

Therefore, a preferred embodiment of the process according to the invention is characterized in that steps a) and b) are carried out simultaneously.

In a further aspect, a process according to the present invention is characterized in that gluconic acid (lactone) is separated during the reaction(s), after a reaction step or at the end of the process, wherein the process for the separation of gluconic acid (lactone) preferably is selected from the group consisting of ion exchange chromatography, electrodialysis, membrane filtration and precipitation by formation of a slightly soluble salt. Appropriate methods are known to a person skilled in the art or, respectively, can be learnt from the relevant literature. An instruction for electrodialysis for the isolation of gluconic acid is provided, for example, in U.S. Pat. No. 6,187,570. Therein, a method is described by means of which derivatives of gluconic acid can be isolated by electrodialysis from a fermentation batch or a cell-free, biocatalytic batch. Between the cathode and the anode, several anion and cation membranes are arranged alternately. The block made of the cathode, the anode and the intermediate membranes is filled with an electrolyte. There are "feed compartments" into which the solution, the fermentation batch or the cell-free, biocatalytic batch is introduced. Furthermore, there are "concentration compartments" in which the acids are concentrated. The two compartments are separated from each other by an anion and a cation membrane. When a voltage is applied, the negatively charged acid migrates through the anion membrane into the concentration compartment, while the uncharged components of the solution remain in the feed compartment. Thus, the gluconic acid or, respectively, the derivatives of this acid is/are separated from neutral components and concentrated.

Regarding the use of ion exchangers for the removal of charged compounds from aqueous solutions, numerous examples exist in the prior art. Specifically for sugar acids, U.S. Pat. No. 3,935,071 and WO2014076012A1 should be mentioned herein.

The process according to the present invention is carried out in an aqueous system, to which a buffer is optionally added. Suitable buffers include, for example, acetate, potassium phosphate, tris-HCl, triethanolamine and glycine buffers, which, for example, have a pH value ranging from 5 to 10.5, preferably from 6 to 10. Additionally or alternatively, the pH value can be controlled via the measurement of the pH value as well as feedback addition of acid(s) or base(s). Additionally or alternatively, ions can be added to the system for stabilizing the enzymes, such as, for example, $Mg^{2+}$ or other additives such as, e.g., glycerol.

Depending on the enzymes used, the process according to the present invention can be carried out at temperatures ranging from 10° C. to 70° C., preferably from 15° C. to 55° C.

Due to the temperature-dependent solubility of D-glucose or possibly of mixtures of D-glucose with other sugars, the glucose/sugar concentration should in any case be adapted to the respective reaction temperature when the process is performed.

Figure 2:
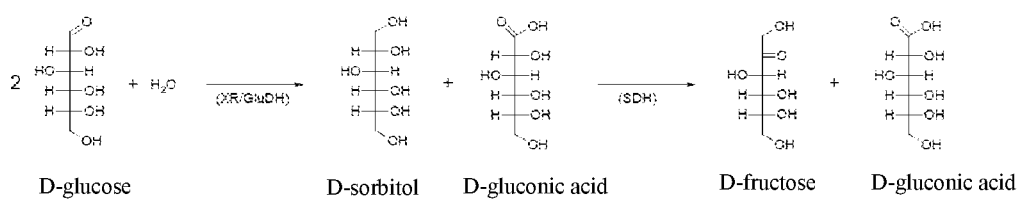
Figure 3:
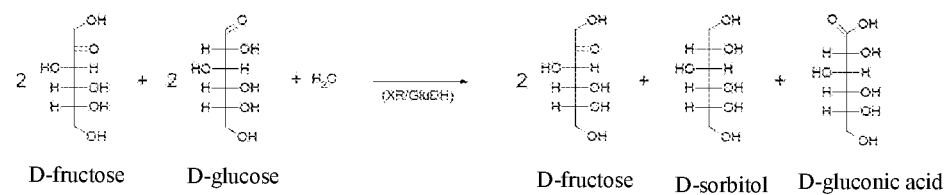
Figure 4:
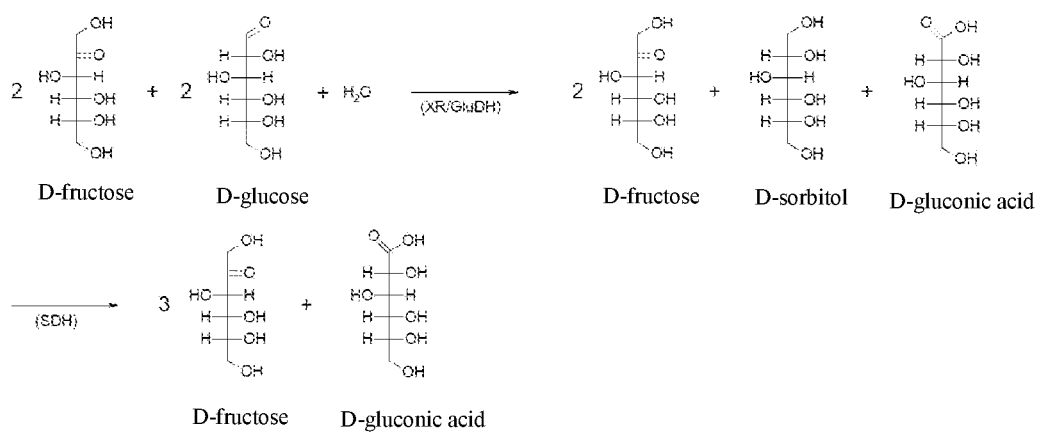
Figure 5:
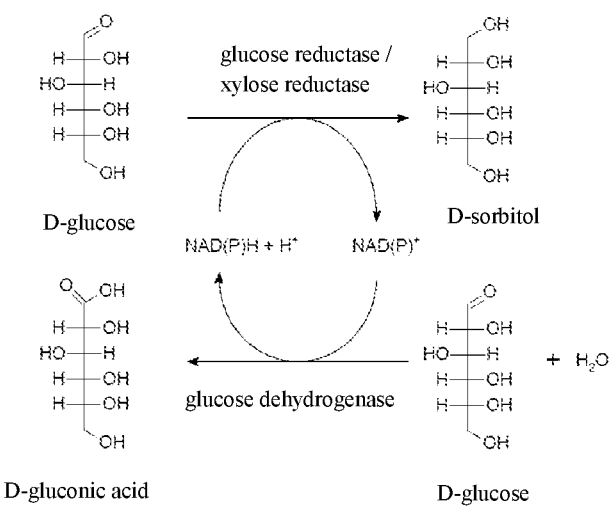

The present invention is characterized in that isomerization of D-glucose is effected by reduction to D-sorbitol, which is oxidized to D-fructose, with a mixture of D-glucose and D-fructose being present at the onset of the reaction. Certain embodiments of this aspect are illustrated in the reaction schemes in FIG. 2 or FIG. 4.

In a process according to the present invention, the enzymatic redox reactions for the conversion of D-glucose to D-sorbitol and D-gluconic acid and for the further conversion of the resulting D-sorbitol to D-fructose are preferably catalyzed by dehydrogenases which use the redox cofactors $NAD^+/NADH$ and/or $NADP^+/NADPH$.

In the context of the present invention, a glucose dehydrogenase is understood to be an enzyme which catalyzes the oxidation of D-glucose to D-gluconic acid (lactone) and, in doing so, reduces an amount of redox cofactor $NAD(P)^+$ to NAD(P)H which is essentially equimolar to the converted amount of D-glucose. To do so, this enzyme does not necessarily have to be annotated as a "glucose dehydrogenase". An enzyme with a different designation may also be used, provided that it has the measurable activity as described. A person skilled in the art is able to examine an enzyme in question for the sought-after activity with a simple photometric test. The literature contains many instructions for measuring the activity of sugar oxidoreductases. In principle, such tests in aqueous solution contain a buffer substance (e.g., potassium phosphate buffer or triethanolamine buffer, for example with a pH value of between pH=6.0 and pH=10.0, in the example pH=7.0-pH=8.0), the enzyme to be examined in the appropriate dilution (herein: glucose dehydrogenase), the substrate in question (herein: D-glucose) at the desired concentration (e.g., 5% (w/v)), the appropriate redox cofactor $NAD(P)+$ or NADPH (in the example of glucose dehydrogenase: $NAD^+$ or $NADP^+$). The result of the reaction is a consumption or the formation of NAD(P)H (herein: formation). This allows the reaction to be monitored photometrically at 340 nm ($\varepsilon = 6220\ M^{-1}\ cm^{-1}$). Based on the reaction kinetics, a person skilled in the art is able to calculate the activity of the enzyme. In this connection, the enzyme unit 1 U corresponds to the amount of enzyme which is required for converting 1 μmol of substrate per minute. A comparison with known enzymes for assessing the suitability of the new enzyme is possible. Analogously, the procedure as described can also be applied to other sugar dehydrogenases.

In the context of the present invention, a glucose reductase is understood to be an enzyme which catalyzes the reduction of D-glucose to D-sorbitol and, in doing so, oxidizes an amount of redox cofactor NAD(P)H to $NAD(P)^+$ which is essentially equimolar to the converted amount of D-glucose. To do so, this enzyme does not necessarily have to be annotated as a "glucose reductase", provided that it has the measurable activity as described. This is particularly the case for enzymes which are annotated as a "xylose reductase", but function also as a glucose reductase. It has already been shown that suitable xylose reductases can be used for reducing D-glucose to D-sorbitol (e.g., Wang X. et al., Biotechnol. Lett., 2007, Volume 29, p. 1409-1412). Furthermore, some enzymes referred to as "aldehyde reductase" are suitable for reducing D-glucose to D-sorbitol (e.g., aldehyde reductase from *Galdieria sulphuraria*, see: Gross W., Seipold P., and Schnarrenberger C. (1997) Characterization and Purification of an Aldose Reductase from the Acidophilic and Thermophilic Red Alga *Galdieria sulphuraria*. Plant Physiol. 114(1), 231-236.).

In the context of the present invention, a sorbitol dehydrogenase is understood to be an enzyme which catalyzes the oxidation of D-sorbitol to D-fructose and, in doing so, preferably reduces an amount of redox cofactor $NAD(P)^+$ to $NAD(P)H$ which is essentially equimolar to the converted amount of D-sorbitol. To do so, this enzyme does not necessarily have to be annotated as a "sorbitol dehydrogenase". An enzyme with a different designation may also be used, provided that it has the measurable activity as described. For example, a xylitol dehydrogenase from *Galactocandida mastotermitis* may be mentioned in this connection. In addition to the eponymous activity, it is also capable of oxidizing sorbitol to fructose.

Suitable enzymes for the reduction of D-glucose to D-sorbitol are known and include, for example, xylose reductases, which are obtainable, for example, from *Candida tropicalis* or *Candida parapsilosis*.

Suitable enzymes for the oxidation of D-glucose to D-gluconic acid are known and include, for example, glucose dehydrogenases, which are obtainable, for example, from *Bacillus subtilis, Bacillus megaterium* or *Thermoplasma acidophilum*.

Suitable enzymes for the oxidation of D-sorbitol to D-fructose are known and include, for example, sorbitol dehydrogenases, which are obtainable, for example, from *Bacillus subtilis, Malta domestica, Rhodobacter sphaeroides* or *Galactocandida mastotermitis*.

In the oxidation of D-sorbitol to D-fructose, redox cofactors that are used are preferably regenerated in the same reaction batch by at least one further redox enzyme, optionally with co-substrate(s) being consumed.

Substances which are reduced or oxidized during the regeneration of $NAD^+/NADH$ and/or $NADP^+/NADPH$ (or other redox cofactors) are referred to as co-substrates. Suitable co-substrates can be used in a process according to the present invention for the oxidation of D-sorbitol to D-fructose and include, for example, ketones (e.g., acetone), aldehydes (e.g., acetaldehyde), pyruvic acid and its salts and/or oxygen. In the conversion of D-glucose to D-sorbitol and D-gluconic acid, no external co-substrate is needed, since the redox cofactors are mutually regenerated by the two reactions.

NAD(P)H oxidases are known to a person skilled in the art. Suitable NAD(P)H oxidases are obtainable, for example, from *Leuconostoc mesenteroides, Streptococcus mutans, Clostridium aminovalericum*. These NAD(P)H oxidases share the property that water emerges as the reaction product. In principle, however, it is also possible to use NAD (P)H oxidases in which hydrogen peroxide $H_2O_2$ emerges as the reaction product. Such enzymes are obtainable, for example, from *Brevibacterium* sp. or *Thermotoga maritima*. This entails the risk that hydrogen peroxide will accumulate and damage enzymes. Therefore, it is common to add a catalase. Said catalase converts $H_2O_2$ into water and oxygen.

Enzymes can be used in a process according to the present invention as such, optionally in the form of cell lysates, optionally as recombinantly overexpressed proteins, for example as proteins recombinantly overexpressed in *E. coli*, wherein, furthermore, the appropriate cell lysates can preferably be used without further purification. Depending on the enzyme to be produced, other microorganisms can also be used for the expression, e.g., microorganisms known to a person skilled in the art. Solid components of the respective microorganisms either can be separated in a process according to the present invention or can be used additionally in the reaction (for example, whole-cell biocatalysts). It is also possible to use culture supernatants or lysates of microorganisms which already exhibit sufficient enzyme activities without recombinant DNA technology. In a process according to the present invention, enzymes as well as redox cofactors can be used either in a soluble form or in the state of being immobilized on solids.

The terms "gluconic acid" and "gluconic acid lactone" are used as synonyms. The mention of one of the terms includes the respective other one. The equilibrium between gluconic acid and gluconic acid lactone in aqueous solutions depends on the pH value of the solution. During a biocatalytic reaction according to the present process, it may be advantageous to keep the pH value constant during the reaction. This can be effected, for example, by an adequate buffer concentration or by a (feedback) addition of acids or bases such as, e.g., sodium hydroxide solution, sodium bicarbonate, sodium carbonate or calcium carbonate.

The mention of an acid or of the salt of an acid herein includes the term not mentioned in the respective case. Herein, the mention of acids also includes all esters derived therefrom. Furthermore, compounds (partially) provided with protective groups are herein included in the mention of the underlying substances.

In a process according to the present invention, D-glucose is usually present in the aqueous reaction mixture at a concentration of ≥5% (w/v) D-glucose, preferably ≥10% (w/v) D-glucose, particularly preferably ≥15% (w/v) D-glucose, wherein a concentration of 50% (w/v), preferably 40% (w/v), particularly preferably 35% (w/v), should not be exceeded. The concentration ranges also apply to the mixture of D-glucose and D-fructose. In this case, the indicated concentrations refer to the sum of all dissolved sugars.

In a particular aspect of the process according to the present invention, the D-glucose portion contained, for example, after the cleavage of sucrose or after the production of glucose-fructose syrup (e.g., by means of glucose isomerase) can be converted by half to D-sorbitol and by half to D-gluconic acid (lactone). D-sorbitol, which is formed, is oxidized further to D-fructose, resulting in an increase in the proportion of D-fructose in the total sugar content.

Gluconic acid (lactone), which is prepared according to a process according to the present invention, can be separated from the reaction mixture. This can occur directly after or during the step in which gluconic acid is produced or only after one or several further enzymatic reactions in the mixture. A person skilled in the art is aware of various methods for this purpose, such as, for example, ion exchange chromatography, electrodialysis, membrane filtration and precipitation by formation of a slightly soluble salt. Those methods are comprehensively described in the literature. In the following, exemplary examples will be described.

In U.S. Pat. No. 6,284,904, a method is described which serves for the removal of organic acids, such as, e.g., succinate, from industrial solutions such as fermentation batches or hydrolysates. In doing so, the solution is passed through an anion exchanger, which is washed under conditions in which the organic acids are not eluted. Subsequently, the organic acids are eluted by adding stronger, inorganic anions. Thus, organic anions can be isolated from a complex solution, such as, for example, a hydrolysate, and can also be concentrated.

In U.S. Pat. No. 6,187,570, a method is described by which derivatives of gluconic acid can be isolated from a fermentation batch or a cell-free, biocatalytic batch by means of electrodialysis. Between the cathode and the anode, several anion and cation membranes are arranged alternately. The block made of the cathode, the anode and the intermediate membranes is filled with an electrolyte. There are "feed compartments" into which the solution, the fermentation batch or the cell-free, biocatalytic batch is introduced. Furthermore, there are "concentration compartments" in which the acids are concentrated. The two compartments are separated from each other by an anion and a cation membrane. When a voltage is applied, the negatively charged acid migrates through the anion membrane into the concentration compartment, while the uncharged components of the solution remain in the feed compartment. Thus, the gluconic acid or, respectively, the derivatives of this acid is/are separated from neutral components and concentrated.

D-fructose produced by a process according to the present invention can be provided, for example, as an aqueous solution such as, e.g., a syrup or can be isolated from the solution. A particular embodiment of the process according to the present invention is characterized in that D-fructose obtained according to the present invention is isolated, in particular in a crystallized form. Instructions for the crystallization of fructose can be learnt from the prior art (e.g., EP 293 680 B1, EP 613 954 B1, U.S. Pat. Nos. 4,895,601, 5,047,088).

In a particular aspect, in a process according to the present invention, the mixture of D-glucose and D-fructose is obtained by enzymatic or non-enzymatic cleavage of sucrose, preferably by enzymatic cleavage of sucrose, for example with an invertase, wherein the enzymatic cleavage of sucrose may occur either in a separate upstream step or in the same reaction batch as the following redox reactions. In this connection, it is possible to first completely cleave the sucrose by means of invertase. It is also possible to perform the redox reactions according to the invention on the released glucose already during the ongoing invertase reaction.

Since D-fructose of very high purity can be produced by the process according to the present invention, this fructose is suitable for further reactions to form basic chemicals. Those chemicals are thus accessible from regenerative sources. One such possible reaction is the production of hydroxymethylfurfural (HMF). The course of such a process can be learnt, for example, from WO 2013/117585 A1. For example, HMF can be converted further to furandicarboxylic acid (FDCA). Methods published in the prior art exist for this purpose (see, e.g., WO 2015/193364 A1). FDCA is an important raw material for the production of polymers from regenerative sources. For example, FDCA can be used for the production of the synthetic material polyethylene furanoate (PEF). Said material can serve as a substitute for polyethylene terephthalate (PET) and is even superior to the latter in some properties. A field of application for PEF is, for example, the production of packaging material such as, for example, bottles, which can be used, for instance, for packaging beverages, cosmetics, detergents, etc.

| Abbreviations | |
|---|---|
| h | hour(s) |
| HPLC | high-performance liquid chromatography |
| IPA | isopropyl alcohol (2-propanol) |
| MeOH | methanol |
| PET | polyethylene terephthalate |
| PEF | polyethylene furanoate |
| RID | refractive index detector |

EXAMPLES

All temperatures are in degrees Celsius (° C.).

Example 1

Conversion of D-Glucose to D-Gluconic Acid (Lactone) and D-Sorbitol in a Mixture Containing D-Fructose The following reaction mixture was prepared: $dH_2O$: balance to 500 µl total volume; 50 mM triethanolamine buffer pH 8.0 (adjusted with HCl); 5% (w/v) D-glucose; 5% (w/v) D-fructose; 0.2 mM $NADP^+$; 5 U xylose reductase (from *Candida parapsilosis*, recombinantly expressed in *E. coli*, cell suspension); 5 U glucose dehydrogenase (from *Bacillus subtilis*, recombinantly expressed in *E. coli*, cell lysate); 10 mg $CaCO_3$. The reaction was carried out in a glass reaction vessel with the lid not completely closed to allow escape of possibly emerging $CO_2$. It was incubated with shaking for 24 h (Eppendorf Thermomix, 25° C., 800 rpm). Analysis was performed by HPLC (Agilent 1200 Series, column: Phenomenex Rezex™ RCM monosaccharide calcium 300×7.8 mm (80° C.), detector: RID (50° C.), eluent: $H_2O$ HPLC grade 0.5 ml/min). It was thereby determined that fructose was still present in the solution at about 5% [w/v]. Based on the resulting sorbitol, the conversion of glucose to >90% was determined (relative to the glucose as originally present). In addition, the formation of gluconic acid was detected.

Example 2

Conversion of D-Sorbitol to D-Fructose in a Mixture Containing D-Gluconate and D-Fructose The following reaction mixture was prepared: $dH_2O$: balance to 500 µl total volume; 50 mM triethanolamine buffer pH 8.0 (adjusted with HCl); 2.5% (w/v) sodium D-gluconate; 2.5% (w/v) D-sorbitol; 5% (w/v) D-fructose (such a composition of fructose, sorbitol and gluconic acid can be obtained, for example, approximately by a reaction according to Example 1); 0.2 mM $NAD^+$; 10 U NADH oxidase (from *Clostridium aminovalericum*, recombinantly expressed in *E. coli*, cell suspension); 12.5 U xylitol dehydrogenase (from *Galactocandida mastotermitis*, herein used as a sorbitol dehydrogenase, recombinantly expressed in *E. coli*, cell suspension). The reaction was carried out in a glass reaction vessel. This was incubated with shaking for 24 h (Eppendorf Thermomix; 20° C.; 800 rpm). In order to allow for the supply of air-oxygen, the reaction vessel was sealed with aluminium foil into which several holes were punched. The analysis was performed as described in Example 1. The conversion of sorbitol to fructose (relative to the sorbitol as originally present) was >99% (w/w). Because of the reaction, the fructose concentration increased to approx. 7.5% (w/v). D-gluconic acid was still contained in the solution.

Example 3—Conversion of a Mixture of Glucose and Fructose into Fructose—Parallel Implementation of the Conversion of Glucose and of the Oxidation of the Resulting Sorbitol in One Pot The following reaction mixture was prepared: ddH$_2$O (ad 500 µl), calcium carbonate (15 mg), 500 mM TEA/NaOH buffer 8.0 (50 µl), glucose (25 mg), fructose (25 mg), 10 mM NAD+ (20 µl), 10 mM NADP+ (10 µl), NADPH-dependent xylose reductase (approx. 4 U), NADP-dependent glucose dehydrogenase (approx. 5 U), NADH-dependent NADH oxidase (approx. 10 U), NAD-dependent sorbitol dehydrogenase (approx. 5 U). The reaction mixture was incubated in a 1.5 ml glass vessel with a gas-permeable lid for 16 h (Eppendorf Thermomixer 20° D, 850 rpm). The reaction products were analyzed by HPLC (Agilent 1200 Series, column Phenomenex Rezex RCM monosaccharides ca 300× 7.8 mm). The fructose concentration increased from initially 5% (w/v) to 6.9% (w/w). In addition, an almost complete consumption of glucose was detected. The intermediate sorbitol could be detected only in traces, for which reason it is to be expected that it kept being continuously converted into the final product fructose.

The invention claimed is:

1. A process for the conversion of D-glucose, comprising a step a) in which a part of the D-glucose is enzymatically oxidized to D-gluconic acid (lactone) and a part of the D-glucose which is essentially equimolar thereto is enzymatically reduced to D-sorbitol, wherein, in addition to D-glucose, D-fructose is also present in the reaction mixture of step a) and wherein the process comprises a further step b) in which D-sorbitol formed from the D-glucose in step a) is enzymatically oxidized to D-fructose.

2. A process according to claim 1, characterized in that the reaction mixture is contacted in step a) with a glucose dehydrogenase and a xylose reductase having glucose reductase activity or with another glucose reductase.

3. A process according to claim 1, characterized in that, in step b), the D-sorbitol is contacted with a sorbitol dehydrogenase for the enzymatic oxidation, whereby D-sorbitol is oxidized to D-fructose.

4. A process according to claim 1, characterized in that the redox cofactor(s) NAD(P)$^+$ and/or NAD(P)H is/are present in the reaction mixture of step a) and/or in the reaction mixture of step b).

5. A process according to claim 1, characterized in that, during the conversion of D-sorbitol to D-fructose, a reduced redox cofactor NAD(P)H, which has been formed in step b), is enzymatically recycled back to its oxidized starting form continuously and in parallel.

6. A process according to claim 1, characterized in that, during the conversion of D-sorbitol to D-fructose, at least one redox cofactor is regenerated in step b) in the same reaction batch by at least one further redox enzyme, whereby co-substrates are consumed or, respectively, hydrogen is produced.

7. A process according to claim 1, characterized in that D-sorbitol is converted to D-fructose in step b) in an enzymatic process, using and regenerating the redox cofactors NAD$^+$/NADH or NADP$^+$/NADPH, wherein, in the regeneration reaction, which converts the reduced redox cofactor back to its original oxidized form, oxygen, an aldehyde, a ketone, a sugar or a compound of the general formula

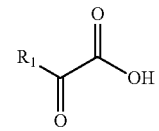

I is reduced, wherein R$_1$ represents a straight-chain or branched-chain (C$_1$-C$_4$)-alkyl group or a (C$_1$-C$_4$)-carboxyalkyl group.

8. A process according to claim 1, characterized in that steps a) and b) occur in the same reaction batch without the intermediate D-sorbitol being isolated.

9. A process according to claim 8, characterized in that steps a) and b) are carried out simultaneously.

10. A process according to claim 1, characterized in that gluconic acid (lactone) is separated during the reaction(s), after a reaction step or at the end of the process.

11. A process according to claim 1, characterized in that D-fructose that is obtained is isolated.

12. A process according to claim 1, characterized in that the mixture of glucose and fructose is obtained by enzymatic or non-enzymatic cleavage of sucrose.

13. A process according to claim 1, characterized in that the amount of D-fructose in the mixture containing D-glucose and D-fructose is between 10% (w/w) and 95% (w/w) based on the total amount of glucose and fructose.

14. A process according to claim 10, wherein the process for the separation of gluconic acid (lactone) is selected from the group consisting of ion exchange chromatography, electrodialysis, membrane filtration, and precipitation by formation of a slightly soluble salt.

15. A process according to claim 12, wherein the mixture of glucose and fructose is obtained by enzymatic cleavage of sucrose by an invertase, wherein the enzymatic cleavage of sucrose occurs either in a separate upstream step or in the same reaction batch as the subsequent redox reactions.

16. A process according to claim 13, characterized in that the amount of D-fructose in the mixture containing D-glucose and D-fructose is between 35% (w/w) and 90% (w/w) based on the total amount of glucose and fructose.

17. A process according to claim 13, characterized in that the amount of D-fructose in the mixture containing D-glucose and D-fructose is between 40% (w/w) and 60% (w/w) based on the total amount of glucose and fructose.

18. A process according to claim 6, wherein the at least one further redox enzyme is selected from the group consisting of alcohol dehydrogenases, sugar dehydrogenases, NAD(P)H oxidases, hydrogenases and lactate dehydrogenases.

19. A process according to claim 6, wherein the co-substrates consumed by the cofactor regeneration reaction are selected from the group consisting of ketones, aldehydes, sugars, pyruvic acid and its salts, oxygen, and mixtures thereof.

20. A process according to claim 11, wherein the D-fructose that is isolated is in a crystallized form.

* * * * *